(12) United States Patent
Pang et al.

(10) Patent No.: US 10,417,794 B2
(45) Date of Patent: Sep. 17, 2019

(54) RECONSTRUCTING CT IMAGE (71) Applicant: Shenyang Neusoft Medical Systems Co., Ltd., Shenyang (CN)

(72) Inventors: Ling Pang, Shenyang (CN); Shanshan Lou, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 146 days.

(21) Appl. No.: 15/833,777

(22) Filed: Dec. 6, 2017

(65) Prior Publication Data
US 2018/0158215 A1 Jun. 7, 2018

(30) Foreign Application Priority Data

Dec. 7, 2016 (CN) .......................... 2016 1 1116515

(51) Int. Cl.
*A61B 6/00* (2006.01)
*G06T 11/00* (2006.01)
*A61B 6/03* (2006.01)
*G01T 7/00* (2006.01)
*G01N 23/046* (2018.01)
(Continued)

(52) U.S. Cl.
CPC ............ *G06T 11/005* (2013.01); *A61B 6/032* (2013.01); *A61B 6/4035* (2013.01); *A61B 6/4266* (2013.01); *A61B 6/542* (2013.01); *A61B 6/545* (2013.01); *A61B 6/585* (2013.01); *G01N 23/046* (2013.01); *G01T 7/005* (2013.01); *H05G 1/34* (2013.01); *H05G 1/36* (2013.01); *G06T 2207/10081* (2013.01); *G06T 2207/30204* (2013.01)

(58) Field of Classification Search
CPC ..... G01N 23/046; G01T 7/005; G06T 11/005; G06T 2207/10081; G06T 2207/30204; A61B 6/032; A61B 6/4035; A61B 6/4266; A61B 6/542; A61B 6/545; A61B 6/585; H05G 1/34; H05G 1/36
See application file for complete search history.

(56) References Cited

U.S. PATENT DOCUMENTS

| 10,206,638 | B2 * | 2/2019 | Nakai | ................... A61B 6/4241 |
| 2015/0160355 | A1 * | 6/2015 | Wang | ...................... G01T 7/005 |
| | | | | 378/19 |
| 2016/0287205 | A1 * | 10/2016 | Zou | ......................... A61B 6/585 |

(Continued)

*Primary Examiner* — Kiho Kim
(74) *Attorney, Agent, or Firm* — McCoy Russell LLP (57) ABSTRACT Methods of reconstructing a CT image and CT devices are provided in examples of the present disclosure. In one aspect, scanning parameters for a CT device is obtained to perform a scan on a subject, a target reference detector is determined from the reference detectors according to the scanning parameters; the scan is performed on the subject according to the scanning parameters to obtain detection data outputted by the detector and reference detection data outputted by the target reference detector; energy data of the original X-rays emitted by the bulb tube with the scanning parameters is determined according to the reference detection data outputted by the target reference detector; the detection data outputted by the detector is corrected based on the energy data of the original X-rays to obtain scanning data; and the CT image of the subject is reconstructed by performing image reconstruction based on the scanning data.

8 Claims, 5 Drawing Sheets (51) Int. Cl.
*H05G 1/34* (2006.01)
*H05G 1/36* (2006.01)

(56) References Cited

U.S. PATENT DOCUMENTS

2017/0184737 A1* 6/2017 Dujmic .................. G01T 7/005
2017/0258412 A1* 9/2017 Daerr ..................... A61B 6/032

* cited by examiner

RECONSTRUCTING CT IMAGE

CROSS REFERENCE TO RELATED APPLICATIONS

This application claims priority to Chinese Patent Application No. 201611116515.3 entitled "Method and Apparatus for Determining Energy Data for Original X-Rays, and CT Device" filed on Dec. 7, 2016, the entire content of which is incorporated herein by reference in its entirety for all purposes.

TECHNICAL FIELD

The present disclosure relates to reconstructing Computed Tomography (CT) image.

BACKGROUND

A detector can be set on a CT device to detect energy of X-rays passing through a subject. Further a reference detector can be set on the CT device to measure energy intensity of original X-rays before the original X-rays are incident onto the subject.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

The terminology used in the present disclosure is for the purpose of describing a particular example only, and is not intended to be limiting of the present disclosure. The singular forms such as "a", "said", and "the" used in the present disclosure and the appended claims are also intended to include multiple, unless the context clearly indicates otherwise. It is also to be understood that the term "and/or" as used herein refers to any or all possible combinations that include one or more associated listed items.

In a CT scanning process, energies of X-rays emitted by a bulb tube may not be exactly consistent with each other due to tube voltage fluctuation even though the X-rays pass through a filter, which can cause a great effect for CT image reconstruction. In an example, energy data of the X-rays measured by the reference detector above may be taken as reference correction data for intensity of the X-rays before the X-rays are incident onto a subject, so as to correct influence on the reconstructed CT image due to the respective different energies of the X-rays emitted by the bulb tube during the scanning process, where the energy data of the X-rays may be expressed by the number of photons of the X-rays.

In an example, the CT device may be set with one or two reference detectors. As an energy distribution range of the X-rays emitted by the bulb tube is expanded on the CT device, there may be two cases as follows when the original X-rays are measured by the reference detector.

In a first case, when a CT device performs a low-dose scan, a resolution of measurement data outputted by the reference detector may be low, which causes that precise correction cannot be performed based on the measurement data in an image reconstruction process.

In a second case, when the CT device performs a high-dose scan, the actual dose of the X-rays may exceed an upper limit of a measurement range of the reference detector above, which causes that the measurement data is not precise, and the precise correction cannot be performed based on the measurement data in the image reconstruction process.

In the two cases above, a quality for the reconstructed CT image is affected and a diagnosis for a disease performed by a doctor based on the CT image can be affected.

In a CT imaging process, a scan is performed on a subject, e.g., a layer with a thickness for a part of a human body, by using an X-ray beam. X-rays penetrating the layer are received by a detector. Energy of the received X-ray is converted into electric signals through photovoltaic conversion. The electric signals are converted into digital signals by an Analog/Digital Converter (ADC) where the digital signals may be referred to as raw data, or may be referred to as projection data. An X-ray attenuation coefficient or an X-ray absorption coefficient for each voxel may be obtained by inputting the raw data into a computer for processing. These coefficients can be arranged into a digital matrix, and each digit in the digital matrix is converted into a small block with a different gray level ranged from black to white, e.g., a pixel, and these pixels are arranged into the matrix to form a CT image. That is, a CT image is a reconstruction image generated based on the raw data obtained by the detector, which may be referred to as a CT reconstruction image in examples of the present disclosure.

A CT device may include two types of detectors. A first type of the detectors measure energy intensity of X-rays passing through a subject (which may be expressed by the number of photons of the X-rays), and another type of the detectors may be referred to as a reference detector which measures energy intensity of original X-rays not passing through the subject. The detection data outputted by both two types of the detectors may be referred to as the raw data above. In a subsequent calculation processing process, the detection data outputted by the reference detector may be taken as reference correction data to correct the detection data of the X-rays passing through the subject in a way that the X-ray attenuation coefficient or the X-ray absorption coefficient can be accurately obtained for each voxel.

The more accurate the detection data of the original X-rays outputted by the reference detector, the more accurate the X-ray attenuation coefficient or the X-ray absorption coefficient for each voxel, further, better a quality of a CT image reconstructed based on the attenuation coefficient or the absorption coefficient.

On this basis, a CT device is provided according to examples of the present disclosure. The CT device includes a bulb tube for generating X-rays, a plurality of reference detectors for detecting X-rays in different scanning dose ranges, a processor, and a mechanism-readable storage medium. The reference detectors detect energy intensity of the X-rays not passing through a subject. The number of the reference detectors may be determined according to a scanning dose distribution range of the X-rays emitted by the bulb tube on the CT device and detection capabilities of the reference detectors. In an example, the scanning dose distribution range of X-rays emitted by the bulb tube is determined by scanning parameters, e.g., a tube voltage, a tube current, and exposure time which are bearable by the bulb tube. When the scanning dose range of the X-rays is large, the number of reference detectors set for the scanning dose range may be determined according to the actual detection capabilities of the detectors.

When both a maximum scanning dose and a minimum scanning dose of the CT device may be detected by a reference detector, the detection data does not affect the quality of the subsequently reconstructed CT image, thus, there is no need to set different reference detectors. If the energy intensity of X-rays arriving at a reference detector is lower than a lower detection limit of the reference detector when the bulb tube performs a low-dose scan, the original X-rays not passing through the subject cannot be precisely measured. If the energy intensity of the X-rays arriving at a reference detector exceeds an upper detection limit of the reference detector when the bulb tube performs a high-dose scan, the detection data outputted by the reference detector may be not accurate. For any of the two cases above, different reference detectors may be set, such that the detection data outputted by at least one reference detector can be used to accurately determine the energy intensity of the original X-rays when the bulb tube performs the scan by using the dose.

In an example, it is assumed as follows. Maximum scanning parameters include a tube voltage of 140 kv, a tube current of 35 mA, and exposure time of 10 s when the bulb tube emits X-rays with a maximum dose, and a theoretical measurement value of a detector corresponding to the maximum dose is 1 million. Further, a minimum scanning parameters include a tube voltage of 60 kv, a tube current of 10 mA, and exposure time of 1 s when the bulb tube emits X-rays with a minimum dose, and a theoretical measurement value of the detector corresponding to the minimum dose is 1.6 thousand. A measurement range of the reference detector is 100 thousand to 800 thousand, thus, the X-rays with the low dose above, e.g., the numerical value 1.6 thousand, cannot be detected by the reference detector. The numerical value which corresponds to the maximum dose and is outputted by the reference detector is 800 thousand, which is wrong, compared with the actual value of 1 million.

In an example of the present disclosure, a plurality of reference detectors, e.g., two reference detectors, may be set based on the cases above, and each reference detector may accurately measure X-rays in a preset dose range. Due to a fixed capacity of a detector, detection channels covered by different reference detectors may be designed based on an example of the present disclosure, such that the reference detectors can accurately measure the detection data of the original X-rays, and the energy data of the original X-rays can be accurately calculated according to the detection data.

Two reference detectors are taken as an example. Respective channels covered by the reference detectors may be designed by a method as follows in a production stage for a CT device.

The above-mentioned dose range of X-rays is divided into two preset dose ranges, for example, a first dose range is 1.6 thousand to 500 thousand and a second dose range is 500 thousand to 1 million.

The channels covered by the reference detectors are set according to the two preset dose ranges. It is assumed that a filter and a reference detector are set in sequence along an incidence path of X-rays on a channel covered by the reference detector.

For the first dose range, a channel covered by a first reference detector may be set in the following at least two methods as follows.

In a first method, a size of the filter on the detection channel covered by the first reference detector may be reduced to reduce a thickness of the filter through which the X-rays pass. In a case that the intensity of the X-rays satisfies a scanning condition, it can be ensured that the number of photons absorbed by the filter from the X-rays is reduced so as to increase the energy of the X-rays arriving at the first reference detector.

In a second method, an auxiliary circuit is added for the first reference detector to enhance generated electric signals after the photons in the X-rays act on a photosensitive component of the first reference detector.

Further, the detection channel covered by the first reference detector may be reasonably designed in combination of the two methods above in a way that the first reference detector can measure the original X-rays with the minimum dose. For example, in the scanning condition that the low dose above is 1.6 thousand, a lower measurement limit of the first reference detector may be adjusted to be 101.6 thousand by at least one of the above method such that the lower measurement limit can be within the measurement range of 100 thousand to 800 thousand for the first reference detector, and the first reference detector can detect the original X-rays with the low dose.

For the second dose range, a detection channel covered by a second reference detector may be set by at least three methods as follows.

In a first method, a size of a filter on the detection channel covered by the second reference detector may be increased to increase a thickness of the filter through which the X-rays pass so as to enhance the absorption effect of the filter for photons in the X-rays. That is, the absorption coefficient of the filter is increased in a way that the energy intensity of the X-rays arriving at the second reference detector is within the measurement range of the second reference detector.

In a second method, an attenuating component, for example, a tungsten or molybdenum component with a preset thickness or an adjustable thickness, is added onto the detection channel covered by the second reference detector to further attenuate the X-rays which passes through the filter in a way that the energy intensity of the X-rays arriving at the second reference detector is within the measurement range of the second reference detector.

In a third method, an auxiliary circuit is added onto the second reference detector, where the auxiliary circuit may weaken the generated electric signals after the X-rays act on a detection component of the second reference detector.

The detection channel covered by the second reference detector may be reasonably designed in combination of the three methods above, such that the second reference detector can measure the original X-rays with the maximum dose. For example, in the scanning condition that the above maximum dose is 1 million, the measurement data corresponding to the maximum dose outputted by the second reference detector may be adjusted to be 750 thousand within the measurement range of 100 thousand to 800 thousand for the second reference detector based on at least one of the ways above, so that the second reference detector can detect the original X-rays with the maximum dose.

In a subsequent calculation processing stage, a processor may accurately calculate the energy intensity of the original X-rays according to the effect of the component added onto the detection channel covered by the reference detector for the energy intensity of the original X-rays (such as, the attenuation coefficient or the absorption coefficient, a circuit amplification factor or a circuit minification factor) and the measurement data outputted by the reference detector. Accordingly, actual X-ray intensity measurement ranges, e.g., X-ray dose ranges, corresponding to different reference detectors may be stored in the processor.

Figure 1:
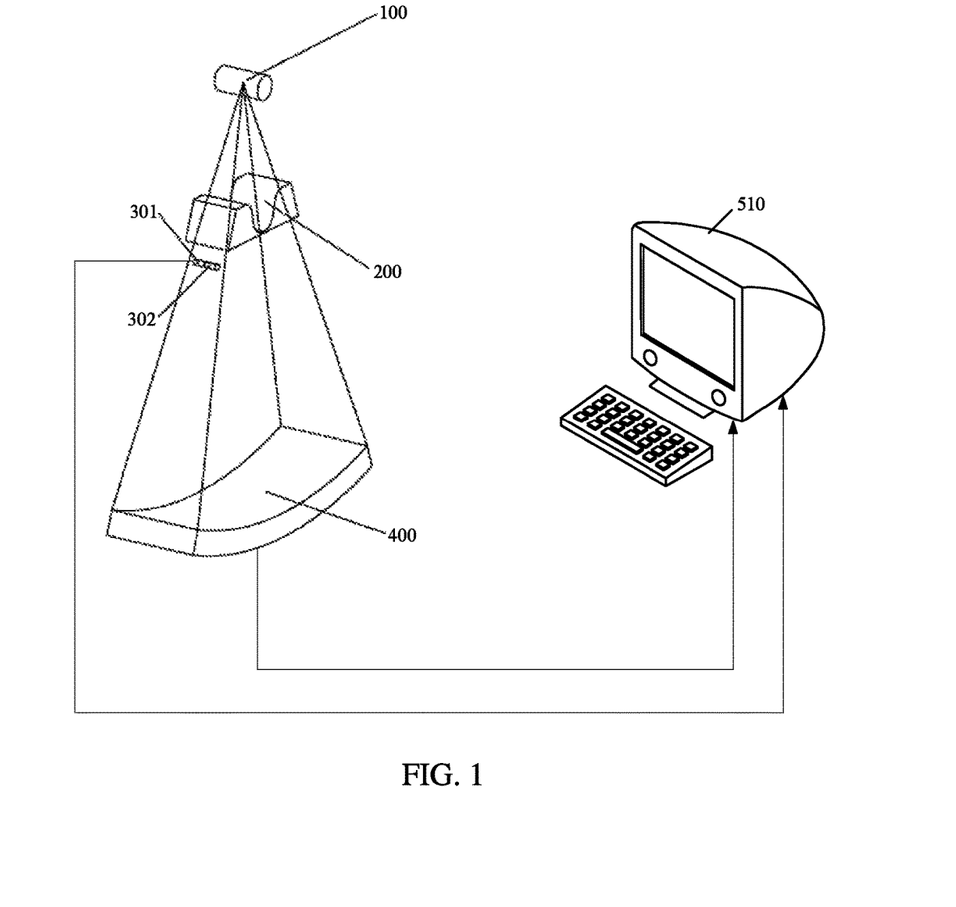
FIG. 1 is a schematic diagram illustrating a CT device according to an example of the present disclosure.

FIG. 1 is a schematic diagram illustrating a CT device according to an example of the present disclosure. The CT device includes a bulb tube 100, a filter 200, a detector 400, a plurality of reference detectors, for example, reference detectors 301 and 302, and a processor 510, where a reference detection channel covered by the reference detector 301 and a reference detection channel covered by the reference detector 302 have different preset scanning dose ranges. Detection data of original X-rays outputted by the reference detectors and data of X-rays which passes through the subject and is detected by the detector 400 are sent together to the processor 510 to be processed in a way that a reconstructed CT image is obtained.

Based on the above CT device set with different reference detectors, a method of determining energy data of original X-rays is provided according to an example of the present disclosure. The method may apply to a processor of a CT device. As described above, the CT device may include a bulb tube for generating X-rays and a plurality of reference detectors. Each reference detector detects original X-rays in a scanning dose range, where the original X-rays are X-rays not passing through a subject.

Figure 2:
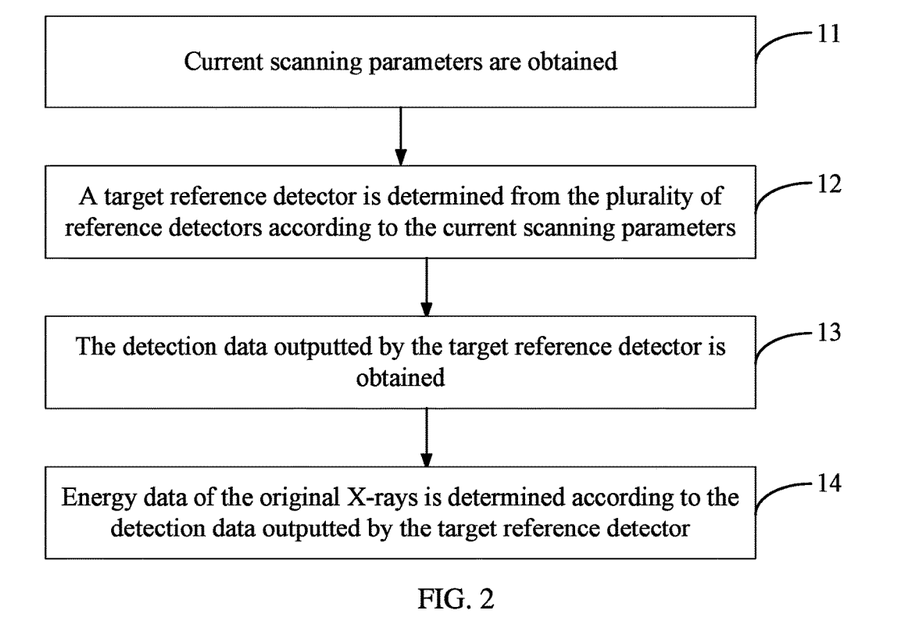
FIG. 2 is a flowchart illustrating a method of determining energy data of original X-rays according to an example of the present disclosure.

FIG. 2 is a flowchart illustrating a method of determining energy data of original X-rays according to an example of the present disclosure. In FIG. 2, the method includes procedures as follows.

At block 11, current scanning parameters are obtained.

In an example, the current scanning parameters may include a tube voltage, a tube current, and exposure time of a bulb tube. A thermal capacity of the bulb tube may be calculated by a product of the three scanning parameters above to estimate a dose of X-rays emitted by the bulb tube.

Before the subject is scanned by using a CT device, the scanning parameters, such as the tube voltage, the tube current, and the like, may be set according to features of the subject, such as age, part, body shape, and the like. The CT device may record scanning time in real time in a way that the processor can calculate a scanning dose according to the obtained scanning parameters.

At block 12, a target reference detector is determined from the plurality of reference detectors according to the current scanning parameters.

The CT device may store a correspondence between each of the reference detectors and a preset scanning dose range. The information above may be configured for the CT device before the CT device leaves a factory.

In an example, the above preset dose range may be expressed as a numerical range of each scanning parameter. Correspondingly, the correspondences between the reference detectors and the preset scanning dose ranges may be recorded in a preset list in Table 1.

TABLE 1

| Detector Identifier | Dose Range |
| --- | --- |
| Detector A | Tube voltage: 60 KV-100 KV<br>Tube current*time of exposure:<br>10 mAs-25 mAs |
| Detector B | Tube voltage: 100 KV-140 KV<br>Tube current*time of exposure:<br>25 mAs-35 mAs |

In the table above, the detector A may be a first reference detector, and the detector B may be a second reference detector.

The process in block 12 above may include querying the Table 1 above based on the current tube voltage and the current product of the tube current and the exposure time to determine the target reference detector.

It is assumed that the current scanning parameters include a tube voltage of 70 kV, a product 20 mAs of the tube current, and the exposure time. The detector A is determined to be the target reference detector by querying the Table 1 above.

In another example of the present disclosure, the preset dose range is expressed as a thermal capacity range of the bulb tube, where the thermal capacity of the bulb tube is equal to the product of the three scanning parameters above, e.g., the thermal capacity of the bulb tube=tube voltage*tube current*exposure time. The thermal capacity may be expressed by Heat Units (HU) where 1 HU is equal to 0.74 J. Correspondingly, the correspondences between the reference detectors and the preset scanning dose ranges may be recorded in a preset list in table 2:

TABLE 2

| Detector Identifier | Dose Range |
| --- | --- |
| Detector A | 0.81 HU-30 kHU |
| Detector B | 30 kHU-66.2 kHU |

Figure 3:
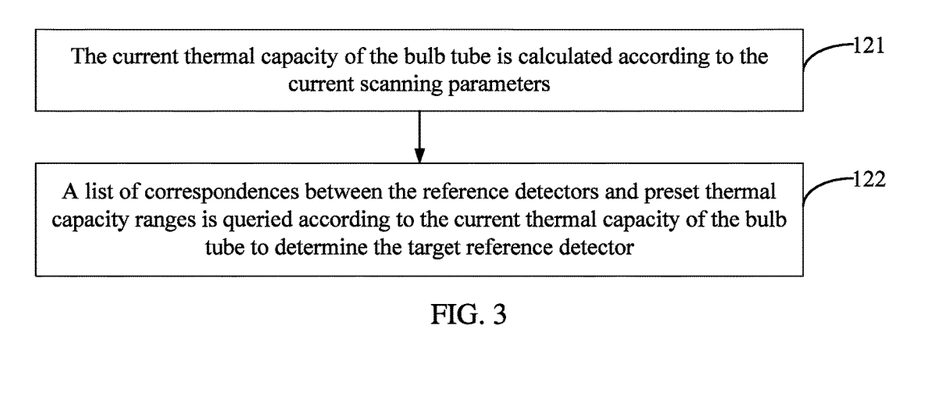
FIG. 3 is a flowchart illustrating a method of determining a target reference detector according to an example of the present disclosure.

In FIG. 3, procedures as follows are included in the block 12 above.

At block 121, the current thermal capacity of the bulb tube is calculated according to the current scanning parameters, where the scanning parameters include the tube voltage, the tube current and the exposure time, and the thermal capacity is equal to the product of the tube voltage, the tube current and the exposure time.

It is still assumed that the current scanning parameters are the tube voltage of 70 kV, and a product 20 mAs of the tube current and the exposure time, the thermal capacity of the bulb tube is equal to 70 kV×20 mAs, i.e., 1.4 kJ. Since 1 J is equal to 0.74 HU, the thermal capacity of the current bulb tube is 1400÷0.74≈1892 HU.

At block 122, a list of correspondences between the reference detectors and preset thermal capacity ranges is queried according to the current thermal capacity of the bulb tube to determine the target reference detector.

When the thermal capacity calculated according to the block 121 above is equal to 1892 HU, the detector A may be determined to be the target reference detector by querying the table 2 above.

At block 13, the detection data outputted by the target reference detector is obtained.

The processor may obtain the detection data outputted by the target reference detector according to the examples above.

In cases described in the examples above, the preset dose ranges corresponding to two reference detectors may be continuous but without intersection. In another example, a CT device may be set with a plurality of reference detectors, and the preset dose ranges corresponding to different reference detectors may be mutually intersected. In other words, the original X-rays emitted by the bulb tube with the scanning parameters may be detected by a plurality of reference detectors. In this case, respective detection data for the plurality of reference detectors may be obtained.

When X-rays with a scanning dose may simultaneously be detected by the reference detector A and the reference detector B, the processor may simultaneously obtain the respectively detection data outputted by the reference detector A and the reference detector B.

At block 14, energy data of the original X-rays is determined according to the detection data outputted by the target reference detector.

In an example, when the processor determines one target reference detector, the processor may calculate the energy data of the original X-rays according to the detection data and influence factors of the component on the channel which include the target reference detector for the original X-rays after the detection data outputted by the target reference detector is obtained, such as an attenuation factor of a filter, an absorption coefficient of an attenuating component, a scaling factor of an auxiliary circuit for electric signals.

Figure 4:
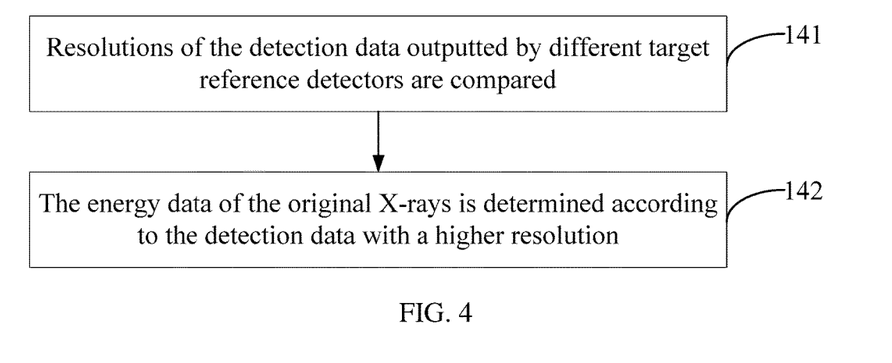
FIG. 4 is a flowchart illustrating a method of determining a target reference detector according to an example of the present disclosure.

When the processor determines two or more target reference detectors, procedures as follows in FIG. 4 are included in the block 14 in FIG. 3 in the case that the two or more target reference detectors are determined.

At block 141, resolutions of the detection data outputted by different target reference detectors are compared.

According to detection principles for a detector, the maximum number of signals which can be obtained by the detector is fixed. More effective signals received, e.g., received photons of X-rays, higher a signal-to-noise ratio of outputted measurement data, e.g., the resolution of the detection data. On the contrary, the less effective the signals received are, the lower the signal-to-noise ratio of the output measurement data, e.g., the resolution of the detection data. Accordingly, the resolution of the detection data output by each reference detector may be sorted.

At block 142, the energy data of the original X-rays is determined according to the detection data with a higher resolution.

In an example, it is assumed that the preset dose range corresponding to the first reference detector is 0.81 HU to 35 kHU, and the preset dose range corresponding to the second reference detector is 30 kHU to 66 kHU. When the current scanning dose is 32 kHU, the original X-rays with the current dose can be simultaneously detected by two reference detectors. The resolution of the detection data outputted by the first reference detector is higher than that outputted by the second reference detector. The energy of the original X-rays is determined according to the detection data outputted by the first reference detector in a way that accurate energy data of the original X-rays can be obtained. Further, the attenuation coefficient for each voxel can be more accurately calculated according to the energy data of the original X-rays example in the subsequent CT image reconstruction process so as to obtain a higher-quality reconstructed CT image.

Methods according to the present disclosure are described above. Devices according to the present disclosure are described below.

Figure 5:
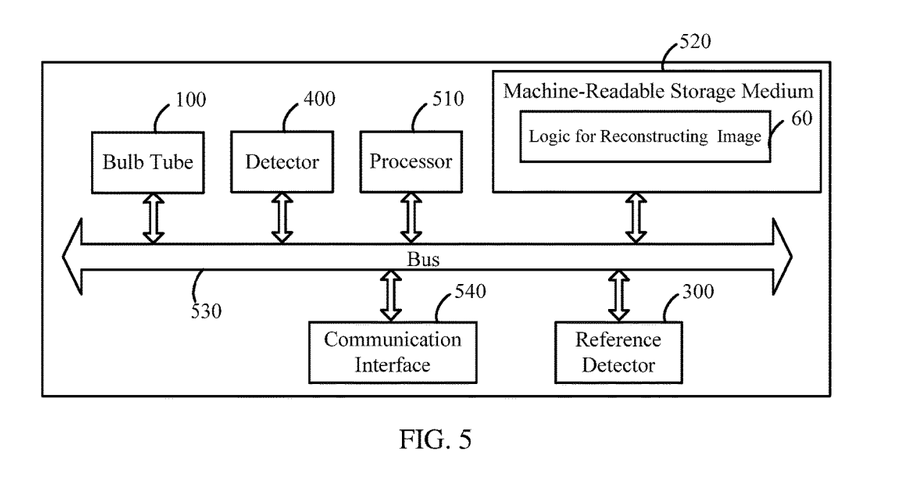
FIG. 5 is a schematic diagram illustrating a structure of a CT device according to an example of the present disclosure.

FIG. 5 schematically illustrates a hardware structure diagram of a CT device, which is provided by an example of the present disclosure. The CT device 50 may include a bulb tube 100, a detector 400, a plurality of reference detectors 300, a processor 510, and a machine-readable storage medium 520, where preset scanning dose ranges for reference detection channels covered by different reference detectors 300 may be different. Detection data of original X-rays outputted by the reference detector 300 and detection data of X-rays which pass through a subject and are detected by the detector 400 are sent together to the processor 510 for processing. A processor 510 and a machine-readable storage medium 520 storing machine executable instructions. The processor 510 may communicate with the machine-readable storage medium 520 via a system bus 530, and execute the method of reconstructing a CT image described above by reading and executing the machine executable instructions corresponding to a control logic 60 for reconstructing a CT image in the machine-readable storage medium 520. The CT device may include a communication interface 540 to communicate with another device.

The machine-readable storage medium 520 mentioned herein may be any electronic, magnetic, optical or other physical storage device and may include or store information, such as executable instructions, data and the like. For example, the machine-readable storage medium 520 may be: a Read-Only Memory (ROM), a volatile memory, a non-volatile memory, a flash memory, a storage drive (e.g. hard disk drive), a solid state harddisk, any type of storage disk (e.g., optical disk, Digital Video Disk (DVD)), or a similar storage medium, or a combination thereof.

Figure 6:
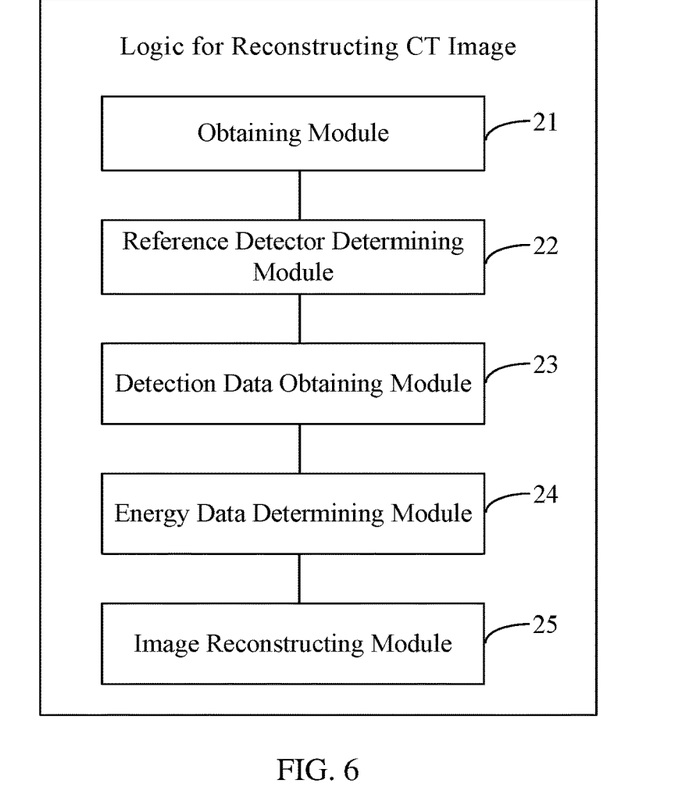
FIG. 6 is a schematic diagram illustrating a structure of logic for reconstructing a CT device according to an example of the present disclosure.

As shown in FIG. 6, functionally, the logic 60 of reconstructing a CT image may include modules as follows.

An obtaining module 21 is configured to obtain scanning parameters for a CT device to perform a scan on a subject.

A reference detector determining module 22 is configured to determine a target reference detector from the plurality of reference detectors according to the scanning parameters.

A detection data obtaining module 23 is configured to perform the scan on the subject according to the scanning parameters to obtain detection data outputted by the detector and reference detection data outputted by the target reference detector.

An energy data determining module 24 is configured to determine energy data of the original X-rays emitted by the bulb tube with the scanning parameters according to the reference detection data outputted by the target reference detector.

An image reconstructing module 25 is configured to correct the detection data outputted by the detector based on the energy data of the original X-rays to obtain scanning data; reconstruct the CT image of the subject by performing image reconstruction based on the scanning data.

Figure 7:
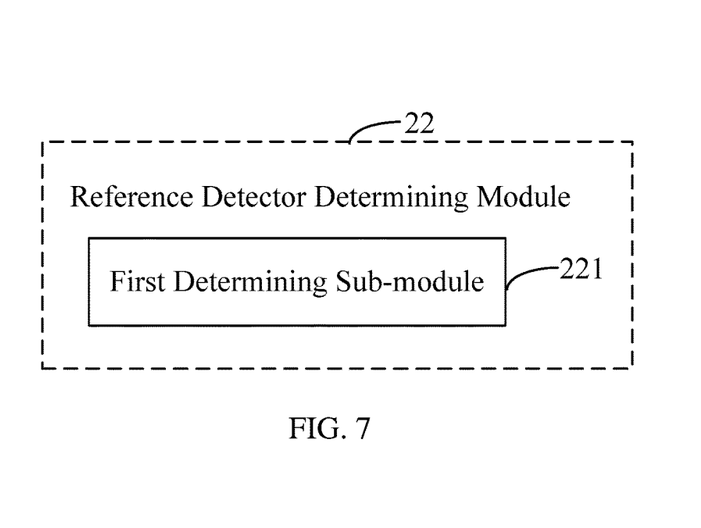
FIG. 7 is a schematic diagram illustrating a structure of a reference detector determining module according to another example of the present disclosure.

FIG. 7 is a schematic diagram illustrating a structure of a reference detector determining module according to an example of the present disclosure. On the basis of the example in FIG. 6, the reference detector determining module 22 may include a first determining sub-module 221.

The first determining sub-module 221 is configured to query a list of correspondences between the reference detectors and scanning parameter ranges based on scanning parameters to determine the target reference detector, wherein the scanning parameters comprise a tube voltage, a tube current, and exposure time.

Figure 8:
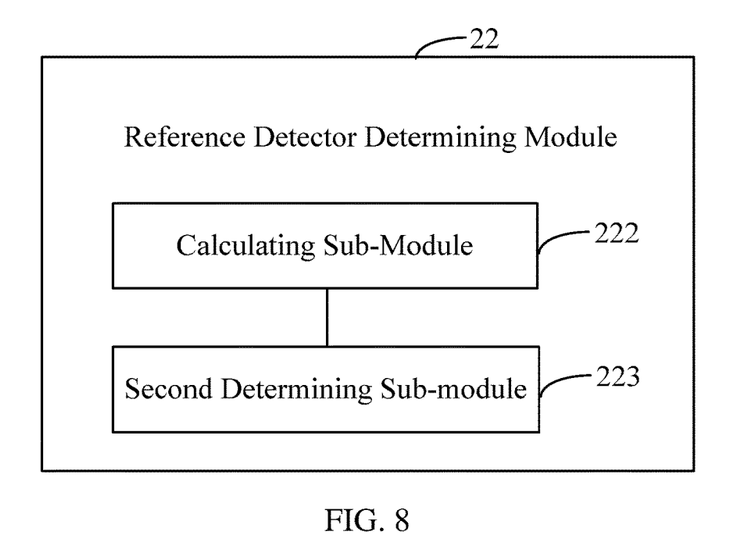
FIG. 8 is a schematic diagram illustrating a structure of a reference detector determining module according to an example of the present disclosure.

FIG. 8 is a schematic diagram illustrating a structure of a reference detector determining module according to another example of the present disclosure. On the basis of the example in FIG. 6, the reference detector determining module 22 may include sub-modules.

The calculating sub-module 222 is configured to calculate a thermal capacity of the bulb tube according to the scanning parameters, wherein the scanning parameters comprise a tube voltage, a tube current and exposure time, the thermal capacity is equal to the product of the tube voltage, the tube current and the exposure time.

The second determining sub-module 223 is configured to query a list of correspondences between the reference detectors and preset thermal capacity ranges according to the thermal capacity of the bulb tube to determine the target reference detector.

Figure 9:
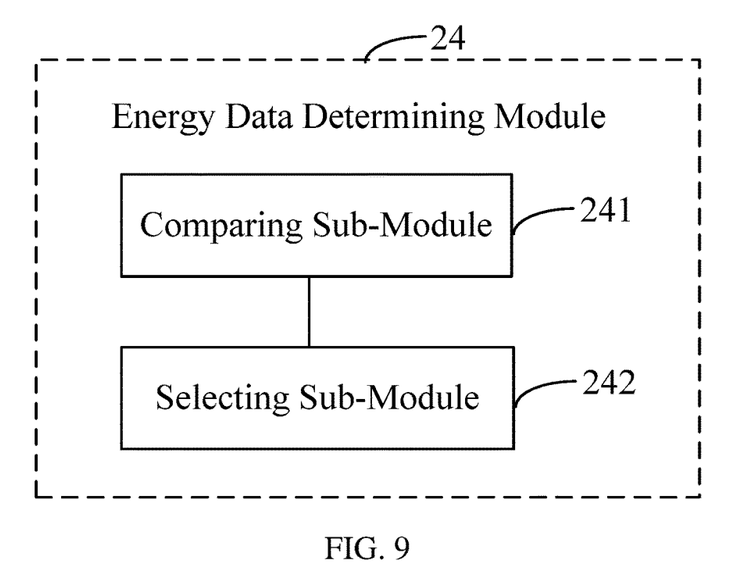
FIG. 9 is a schematic diagram illustrating a structure of an energy data determining module according to an example of the present disclosure.

FIG. 9 is a schematic diagram illustrating a structure of an energy data determining module according to an example of the present disclosure. On the basis of the example shown in FIG. 6, the energy data determining module 24 may include sub-modules as follows.

A comparing sub-module 241 is configured to perform comparison on resolutions of respective reference detection data outputted by the target reference detectors.

A selecting sub-module 242 is configured to determine the reference detection data with a high resolution to be the energy data of the original X-rays.

Since the apparatus embodiments substantially correspond to the method embodiments, a reference may be made to part of the descriptions of the method embodiments for the related part. The apparatus embodiments described above are merely illustrative, where the units described as separate members may be or not be physically separated, and the members displayed as units may be or not be physical units, i.e., may be located in one place, or may be distributed to a plurality of network units. Part or all of the modules may be selected according to actual requirements to implement the objectives of the solutions in the embodiments. Those of ordinary skill in the art may understand and carry out them without creative work.

As can be seen from the above examples, when an energy distribution range of a CT device is large, the detection data of the original X-rays at different dose ranges may be obtained through different reference detectors so as to improve the resolution of the detection data of the X-rays. Further, the energy data of the original X-rays can be determined according to the detection data with a higher resolution. In the subsequent CT image reconstruction process, the processor can accurately calculate the attenuation coefficient of each voxel according to the above energy data of the X-rays such that the quality of the reconstructed CT image can be improved, thereby providing accurate basis for a diagnosis performed subsequently based on the reconstructed CT image.

After considering the specification and practicing the present disclosure, the persons of skill in the prior art may easily conceive of other implementations of the present disclosure. The present disclosure is intended to include any variations, uses and adaptive changes of the present disclosure. These variations, uses and adaptive changes follow the general principle of the present disclosure and include common knowledge or conventional technical means in the prior art not disclosed in the present disclosure. The specification and examples herein are intended to be illustrative only and the real scope and spirit of the present disclosure are indicated by the claims of the present disclosure.

It shall be understood that the present disclosure is not limited to the precise structures described above and shown in the accompanying drawings and may be modified or changed without departing from the scope of the present disclosure. The scope of protection of the present disclosure is limited only by the appended claims.

The invention claimed is:

1. A method of reconstructing a Computed Tomography (CT) image, comprising:
    obtaining scanning parameters for a CT device to perform a scan on a subject, wherein the CT device comprises a bulb tube, a detector, and a plurality of reference detectors, where each of the plurality of reference detectors detects original X-rays in a preset dose range, and where the original X-rays are X-rays not passing through the subject;
    determining a target reference detector from the plurality of reference detectors according to the scanning parameters;
    performing the scan on the subject according to the scanning parameters to obtain detection data outputted by the detector and reference detection data outputted by the target reference detector;
    determining energy data of the original X-rays emitted by the bulb tube with the scanning parameters according to the reference detection data outputted by the target reference detector;
    correcting the detection data outputted by the detector based on the energy data of the original X-rays to obtain scanning data; and
    reconstructing the CT image of the subject by performing image reconstruction based on the scanning data.

2. The method of claim 1, wherein the scanning parameters comprise a tube voltage, a tube current, and exposure time; and wherein the process of determining the target reference detector from the plurality of reference detectors according to the scanning parameters comprises:
querying a list of correspondences between the plurality of reference detectors and scanning parameter ranges based on the scanning parameters to determine the target reference detector.

3. The method of claim 2, wherein when a plurality of target reference detectors are determined, the process of determining the energy data of the original X-rays emitted by the bulb tube with the scanning parameters according to the reference detection data outputted by the target reference detector comprises:
performing a comparison on resolutions of respective reference detection data outputted by the target reference detectors; and
determining the reference detection data with a high resolution to be the energy data of the original X-rays.

4. The method of claim 1, wherein determining the target reference detector from the plurality of reference detectors according to the scanning parameters comprises:
calculating a thermal capacity of the bulb tube according to the scanning parameters, wherein the scanning parameters comprise a tube voltage, a tube current, and exposure time, the thermal capacity is equal to the product of the tube voltage, the tube current and the exposure time; and
querying a list of correspondences between the reference detectors and preset thermal capacity ranges according to the thermal capacity of the bulb tube to determine the target reference detector.

5. A CT device, comprising:
a bulb tube;
a detector;
a plurality of reference detectors, wherein each of the plurality of reference detectors detects original X-rays within a preset dose range, the original X-rays are X-rays not passing through a subject;
a processor, and
a non-transitory machine-readable storage medium storing machine executable instructions which are executable by the processor to:
obtain scanning parameters for the CT device to perform a scan on a subject;
determine a target reference detector from the plurality of reference detectors according to the scanning parameters;
perform the scan on the subject according to the scanning parameters to obtain detection data outputted by the detector and reference detection data outputted by the target reference detector;
determine energy data of the original X-rays emitted by the bulb tube with the scanning parameters according to the reference detection data outputted by the target reference detector;
correct the detection data outputted by the detector based on the energy data of the original X-rays to obtain scanning data; and
reconstruct the CT image of the subject by performing image reconstruction based on the scanning data.

6. The CT device of claim 5, wherein the processor is further caused by the machine-executable instructions to:
query a list of correspondences between the reference detectors and scanning parameter ranges based on scanning parameters to determine the target reference detector, wherein the scanning parameters comprise a tube voltage, a tube current, and exposure time.

7. The CT device of claim 6, wherein when a plurality of target reference detectors are determined, the processor is caused by the machine-executable instructions to:
perform a comparison on resolutions of respective reference detection data outputted by the target reference detectors; and
determine the reference detection data with a high resolution to be the energy data of the original X-rays.

8. The CT device of claim 5, wherein the processor is caused by the machine-executable instructions to:
calculate a thermal capacity of the bulb tube according to the scanning parameters, wherein the scanning parameters comprise a tube voltage, a tube current, and exposure time, where the thermal capacity is equal to the product of the tube voltage, the tube current, and the exposure time; and
query a list of correspondences between the reference detectors and preset thermal capacity ranges according to the thermal capacity of the bulb tube to determine the target reference detector.

* * * * *